US010945667B2

(12) United States Patent
Van Den Heuvel et al.

(10) Patent No.: US 10,945,667 B2
(45) Date of Patent: Mar. 16, 2021

(54) RESTRAINT MANAGEMENT

(71) Applicant: KONINKLIJKE PHILIPS N.V., Eindhoven (NL)

(72) Inventors: Teun Van Den Heuvel, Eindhoven (NL); Yingrong Xie, Eindhoven (NL); Adrienne Heinrich, Den Bosch (NL); Thomas Falck, Aachen (DE); Esther Marjan Van Der Heide, 's-Hertogenbosch (NL); Harald Greiner, Nufringen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 722 days.

(21) Appl. No.: 15/552,906

(22) PCT Filed: Mar. 15, 2016

(86) PCT No.: PCT/EP2016/055483
§ 371 (c)(1),
(2) Date: Aug. 23, 2017

(87) PCT Pub. No.: WO2016/150750
PCT Pub. Date: Sep. 29, 2016

(65) Prior Publication Data
US 2018/0032694 A1    Feb. 1, 2018

(30) Foreign Application Priority Data
Mar. 23, 2015    (EP) .................................... 15160212

(51) Int. Cl.
*A61B 5/11*    (2006.01)
*G16H 40/60*    (2018.01)
(Continued)

(52) U.S. Cl.
CPC .......... *A61B 5/6831* (2013.01); *A61B 5/1114* (2013.01); *A61B 5/1116* (2013.01); *A61B 5/1128* (2013.01); *A61B 5/4809* (2013.01); *A61B 5/4848* (2013.01); *A61B 5/746* (2013.01); *A61G 7/05* (2013.01); *A61G 7/0507* (2013.01); *G06N 5/046* (2013.01); *G06N 20/00* (2019.01);
(Continued)

(58) Field of Classification Search
CPC ... G06F 19/3418; G06F 19/321; G06N 20/00; G06N 5/046; G16H 10/60; G16H 50/20; A61B 5/1114; A61B 5/1116; A61B 5/1128; A61B 5/4809; A61B 5/4848; A61B 5/6831; A61B 5/746; A61B 5/02; A61B 5/0816; A61B 5/165; A61B 2505/03; A61B 2505/07; A61G 7/05; A61G 7/0507
USPC ......................................................... 700/302
See application file for complete search history.

(56) References Cited

U.S. PATENT DOCUMENTS

| | | | |
|---|---|---|---|
| 5,649,541 A | 7/1997 | Stuckey | |
| 5,826,216 A * | 10/1998 | Lyons | ..................... G01S 13/34 702/143 |
| 7,389,552 B1 * | 6/2008 | Reed | ..................... A61G 1/013 296/20 |
| 10,271,768 B1 * | 4/2019 | Murali | ................. A61B 5/0488 |
| 2005/0083207 A1 * | 4/2005 | Smith | ................... A61F 5/3776 340/668 |

(Continued)

*Primary Examiner* — Jason D Mitchell

(57) ABSTRACT

There is provided a restraint management apparatus. The restraint management apparatus comprises a processing unit arranged to: receive one or more types of sensor data; determine a status of a subject based on the received sensor data; determine, based on the determined subject status, a restraint parameter for a restraint device configured to restrain a body part of the subject; and output a signal based on the determined restraint parameter.

15 Claims, 2 Drawing Sheets

(51) Int. Cl.
*A61B 5/00* (2006.01)
*G06N 20/00* (2019.01)
*A61G 7/05* (2006.01)
*G06N 5/04* (2006.01)
*A61B 5/16* (2006.01)
*G16H 50/20* (2018.01)
*A61B 5/02* (2006.01)
*A61B 5/08* (2006.01)
*G16H 10/60* (2018.01)

(52) U.S. Cl.
CPC ............... G16H 40/60 (2018.01); *A61B 5/02* (2013.01); *A61B 5/0816* (2013.01); *A61B 5/165* (2013.01); *A61B 2505/03* (2013.01); *A61B 2505/07* (2013.01); *A61B 2562/0204* (2013.01); *A61B 2562/0219* (2013.01); *A61B 2562/0247* (2013.01); *A61B 2562/0261* (2013.01); *A61G 2203/34* (2013.01); *G16H 10/60* (2018.01); *G16H 50/20* (2018.01)

(56) References Cited

U.S. PATENT DOCUMENTS

| | | |
|---|---|---|
| 2007/0288263 A1 | 12/2007 | Rodgers |
| 2008/0023246 A1* | 1/2008 | Gillet ................. B60R 21/0132 180/268 |
| 2011/0202495 A1* | 8/2011 | Gawlick ................. G16H 50/20 706/59 |
| 2013/0000653 A1* | 1/2013 | Vanderpool ........... A61F 5/3723 128/878 |
| 2013/0127620 A1 | 5/2013 | Siebers |
| 2014/0081654 A1 | 3/2014 | Bechtel |
| 2014/0235969 A1 | 8/2014 | Van Der Heide |
| 2014/0343968 A1 | 11/2014 | Wilson |
| 2014/0345060 A1 | 11/2014 | Ribble |
| 2014/0379224 A1* | 12/2014 | Hyde ................... A61G 5/1056 701/49 |
| 2017/0136265 A1* | 5/2017 | Hyde ................... A61B 5/1121 |
| 2017/0156662 A1* | 6/2017 | Goodall ................. G16H 50/30 |
| 2018/0185240 A1* | 7/2018 | von Schenck ....... A61H 31/006 |

* cited by examiner

RESTRAINT MANAGEMENT

CROSS REFERENCE TO RELATED APPLICATIONS

This application is the U.S. National Phase application under 35 U.S.C. § 371 of International Application No. PCT/EP2016/05483, filed Mar. 15, 2016, published as WO 2016/150750 on Sep. 29, 2016, which claims the benefit of European Patent Application Number 15160212.5 filed Mar. 23, 2015. These applications are hereby incorporated by reference herein.

TECHNICAL FIELD OF THE INVENTION

The invention relates to a restraint management apparatus and method for use in restraining a subject, and in particular relates to a restraint management apparatus and method for use in conjunction with a medical restraint system.

BACKGROUND TO THE INVENTION

In clinical environments such as hospitals and care homes, it is sometimes necessary to restrain a subject, e.g. by fixating them to their bed by means of restraining straps or the like. Use of such restraints may be required, for example, when patients (subjects) become very active due to a certain disease (e.g. one which causes delirium), such that they risk injuring themselves or dislodging or damaging medical equipment such as IV lines, endotracheal tubes or feeding tubes. Some subjects may not be permitted to get out of bed without assistance, for instance because they are connected to medical equipment and/or because they are at a high risk of falling over if they attempt to do so. It is therefore an important patient safety issue to restrain certain subjects when necessary. Currently, restraining straps are applied manually by medical staff. However; with current systems changing restraint parameters such as range/length (i.e. the freedom of movement the restraining straps permit the subject) requires manual intervention by a caregiver, and this means that the restraint parameters are normally kept the same for the whole period during which the restraints are in place.

Decisions about when to apply/release restraints for a given patient are made by medical staff based on their observations. However; it is generally not possible for medical staff to observe every subject in their care, all of the time. This means that there are times when a subject's restraint status is not appropriate to their current condition (e.g. they remain restrained even when lying quietly, they are not restrained whilst moving violently, they are restrained with too great or too little freedom of movement for their current condition).

There is therefore a need for a system which can reduce the amount of time for which a subject is inappropriately restrained. Preferably such a system would be able to achieve a more optimal balance between the clinical need to ensure the safety of the subject and the subject's need to be comfortable and free to move.

SUMMARY OF THE INVENTION

According to a first aspect of the invention, there is provided a restraint management apparatus. The restraint management apparatus comprises a processing unit arranged to: receive one or more types of sensor data; determine a status of a subject based on the received sensor data; determine, based on the determined subject status, a restraint parameter for a restraint device configured to restrain a body part of the subject; and output a signal based on the determined restraint parameter.

Thus, embodiments of the invention advantageously provide an automatic way to predict when a given subject should be restrained, released, or allowed more or less freedom of movement, based on the detected condition of the subject. This creates the possibility of automatically updating restraint parameters in real time, in response to changes in a subject's condition. Thus, an optimum balance between the clinical need to ensure the safety of the subject and the subject's need to be comfortable and free to move can be achieved.

In some embodiments the processing unit is further arranged to receive one or more types of non-sensor data relating to the subject. In some such embodiments the processing unit is arranged to determine a status of a subject based additionally on the received non-sensor data. In some embodiments the one or more types of non-sensor data comprises data originating from a caregiver. In some such embodiments the one or more types of non-sensor data comprises data manually input by a caregiver to the restraint management apparatus or to a device in communication with the restraint management apparatus.

In some embodiments the processing unit comprises a memory containing one or more predefined signatures, each predefined signature relating to a particular type of feature. In some such embodiments the processing unit is arranged to determine a status of a subject by comparing the received data to the one or more predefined signatures to detect one or more features in the received sensor data.

In some embodiments the processing unit is arranged to determine a status of a subject by determining one or more of: a physiological condition of the subject, a position of the subject; a position of a body part of the subject; a movement level of a body part of the subject; an activity level of the subject; whether the subject is asleep or awake; whether the subject's eyes are open; whether the subject is delirious; whether movement of a body part of the subject meets a predefined criterion; whether movement of the subject meets a predefined criterion.

In some embodiments the processing unit is arranged to determine a status of a subject such that the determined status comprises a status value for one or more factors. In some such embodiments status value comprises one or more of: a descriptive indication; a numerical score; a non-numerical level indication.

In some embodiments the processing unit comprises a memory containing rules relating subject status values to restraint parameters. In some such embodiments the processing unit is arranged to determine a restraint parameter by applying one or more of the rules to the determined subject status value. In some such embodiments the processing unit comprises a machine learning module and the rules have been generated by the machine learning module based on historical data relating to the subject. In some embodiments the processing unit is arranged to receive a restraint parameter which has been manually-input to a restraint device, and the machine learning module is arranged to update the generated rules based on the received manually-input restraint parameter.

In some embodiments the processing unit is arranged to determine a restraint parameter such that the determined restraint parameter comprises one of: activation of a restraint device; inactivation of a restraint device; activation of a given restraining component of a restraint device; inactivation of a given restraining component of a restraint device; tightness of a given restraining component of a restraint device; length of a given restraining component of a restraint device; duration of activation of a restraint device; duration of activation of a given restraining component of a restraint device.

In some embodiments the processing unit is arranged to output a signal comprising one or more of: a control signal to an automated restraint device arranged to cause the automated restraint device to apply the determined restraint parameter; a signal to a device associated with a caregiver, the signal comprising an instruction to the caregiver to implement the determined restraint parameter; a control signal to an alarm module of the restraint management apparatus arranged to cause the alarm module to generate an alarm in dependence on the determined restraint parameter; a control signal to a display module of the restraint management apparatus arranged to cause the display module to display information in dependence on the determined restraint parameter; a control signal to a subject feedback module arranged to cause the subject feedback module to generate a message to the subject; a control signal to a lighting module arranged to cause the lighting module to activate a light. In some embodiments the processing unit is arranged to output the signal after a predefined amount of time has passed since the processing unit last output a signal of the same type as the signal.

The invention also provides, according to a second aspect, a restraint system. The restraint system comprises a restraint management apparatus according to the first aspect; and a restraint device configured to restrain a body part of a subject. The restraint device is arranged to: receive a signal output by the restraint management apparatus, and in response to a signal received from the restraint management apparatus, apply a restraint to the subject or alter a parameter of a restraint applied to the subject.

In some embodiments the restraint device is further arranged to: receive a manually-input restraint parameter; in response to a signal received from the restraint management apparatus, apply a restraint to the subject or alter a parameter of a restraint applied to the subject; and transmit a signal containing the manually-input restraint parameter to the restraint management apparatus.

The invention also provides, according to a third aspect, a method for use in restraining a subject. The method comprises: receiving one or more types of sensor data; determining a status of a subject based on the received sensor data; and determining, based on the determined subject status, a restraint parameter for a restraint device configured to restrain a body part of the subject.

In some embodiments the received sensor data comprises one or more of: an image including a subject; an image including a subject and one or more objects in the vicinity of the subject; audio data including sounds generated by a subject; accelerometer data obtained by an accelerometer worn by a subject; measurements of one or more physiological characteristics of a subject; restraint-related data obtained by a sensor associated with a restraint device; pressure data obtained by a bed sensor; bed rail position data obtained by a bed rail sensor.

In some embodiments the received sensor data comprises an image including a subject and one or more objects. In some such embodiments determining a status of a subject comprises: determining a position of a body part of the subject; determining a position of an object in the image; calculating a distance between the body part and the object; and comparing the calculated distance to a predetermined threshold.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE PREFERRED EMBODIMENTS

Figure 1:
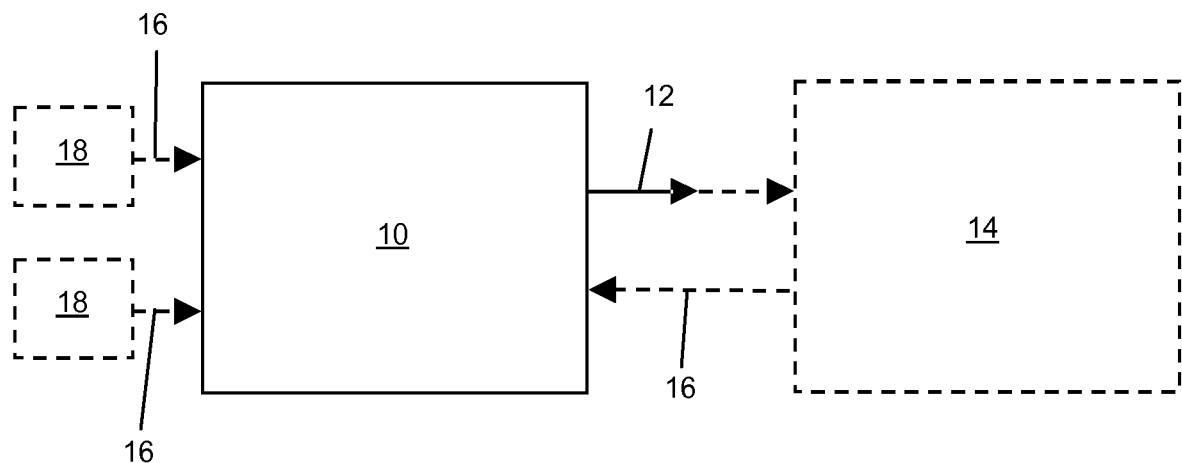
FIG. 1 is an illustration of a restraint management apparatus according to a general embodiment of the invention.

FIG. 1 shows a restraint management apparatus 10 according to an embodiment of the invention. The restraint management apparatus 10 is for use with a restraint device 14 configured to restrain a body part of a subject. In embodiments the restraint device 14 is configured to provide a controllable resistance to movement of a body part. The restraint management apparatus 10 comprises a processing unit. In some embodiments the restraint management apparatus also comprises one or more functional modules, e.g. an alarm module, a display module, a communications module, a user input module, a subject feedback module to present messages to the subject (e.g. audio or text messages), a lighting module to illuminate the subject and/or their surroundings, etc. The processing unit of the restraint management apparatus 10 is arranged to receive one or more types of sensor data 16. In some embodiments the processing unit is arranged to receive sensor data 16 from one or more sensor devices 18. Each sensor device 18 can be, e.g., a camera, microphone, accelerometer, medical monitoring device, or any other type of sensor device arranged to collect sensor data relating to a subject. In some embodiments the processing unit is arranged to receive sensor data from the restraint device 14. In some embodiments the processing unit is arranged to receive sensor data from a user input module of the restraint management apparatus (e.g. where a caregiver has manually input readings obtained by a sensor), and/or a communications module of the restraint management apparatus (e.g. where sensor data is sent to the restraint management apparatus from a remote electronic device, such as a laptop or smartphone of a caregiver). In some embodiments the processing unit is arranged to receive sensor data in real time. In alternative embodiments the processing unit is arranged to receive sensor data at periodic intervals, e.g. in response to a request sent from the processing unit to a sensor device 18 or the restraint device 14.

In some embodiments the processing unit is further arranged to receive non-sensor data, which may or may not be related to the subject. Subject-related non-sensor data can comprise, for example, historical subject information, medical test results, diagnoses, etc. Non-subject related non-sensor data can comprise, for example, software updates, information relating to a restraint device, or any other type of information/data that may be used by the restraint management apparatus. In some embodiments the non-sensor data comprises a manually-input restraint parameter which has been input to a restraint device by a caregiver. It will be appreciated that manually-input data comprises any data received by a device which originates from a caregiver or other human. Manually-input data can, but need not, be input via an input interface of the device receiving the data. Manually-input data can also be input via a remote device in communication with the device receiving the data. Non-sensor data may be received in any of the manners described above in relation to the sensor data.

The processing unit is further arranged to determine a status of a subject based on the received sensor data (and, in some embodiments, received non-sensor data). The determined status should be related to the restraint requirements of the subject, and will generally therefore be indicative of a current or expected amount/type of activity/movement of the subject. In some embodiments the processing unit is arranged to determine a status of a subject by determining one or more of: a physiological condition of the subject, a position of the subject; a position of a body part of the subject; a movement level of a body part of the subject; an activity level of the subject; whether the subject is asleep or awake; whether the subject's eyes are open; whether the subject is delirious; whether movement of a body part of the subject meets a predefined criterion (e.g. defined such that only unusual movement will meet the criterion); whether movement of the subject meets a predefined criterion (e.g. defined such that only unusual movement will meet the criterion).

Various techniques for extracting physiological, position and/or activity information from sensor data are known in the art. For example, data from an accelerometer mounted on the subject, and/or from a pressure sensor mounted on their hospital bed can be analyzed to determine the position of a subject and/or whether and to what extent the subject is moving. Subject movement can also be determined from image data acquired by a camera, using video analysis techniques. Image data can be used to determine the proximity of a body part of a subject to a medical device or other object (e.g. a wall, bed rail, item of furniture, etc.) Audio data collected by a microphone can detect vocalizations, movement noises and/or impact noises generated by the patient, which can be used to determine whether they are in distress, likely to attempt to get out of bed, and/or are at risk of harming them self. Physiological data (e.g. heart rate, respiration rate, breathing pattern, ECG data) can be used in the determination of the status of a subject, e.g. by indicating whether the subject is asleep or awake, indicating which sleep stage the subject is in, and/or indicating whether they are experiencing increased circulatory effort (which can result from increased activity).

In some embodiments the processing unit is arranged to determine the status of a subject by detecting patterns and/or features in the received sensor data. For example, in some embodiments signatures and/or patterns associated with features of interest (such as a particular body part in an image of the subject; a particular object in an image of the subject; a vocalization in an audio recording of the subject; an impact sound in an audio recording of the subject; a peak in accelerometer data, etc.) are stored in a memory associated with the processing unit, and the processing unit is arranged to determine the status of a subject by comparing detected patterns/features with the stored signatures/patterns. In some embodiments the determination is performed based on received sensor data from a particular instant in time (i.e. the determination uses a static analysis). In some embodiments the determination is performed using received sensor data covering a time period (i.e. the determination uses a dynamic analysis). In some embodiments determining the status of a subject comprises tracking a detected feature over a time period. In some embodiments determining the status of a subject comprises detecting movement of a body part of the subject. In some such embodiments, detected movements are classified as being one or more of several different predefined movement types. Any suitable known signal analysis and feature extraction techniques may be used in the performance of step 202.

In a particular embodiment in which the received sensor data 16 comprises image data containing the subject and their immediate surroundings, the processing unit is arranged to determine the status of the subject by detecting, using image analysis techniques, the relative positions of body parts of the subjects and objects. The detected body parts can comprise, for example, one or more of a hand, a foot, the head, etc. The detected objects can comprise, for example, one or more of a patient monitor, an IV stand, a bed rail, a bedside table, etc. In some such embodiments the processing unit is arranged to calculate distances between the detected body parts and the detected objects. In some such embodiments the processing unit is arranged to compare the calculated distances to a predefined threshold. The subject status may then be determined in dependence on the result(s) of the comparing. For example, in some embodiments a status indicating that restraint of a body part is required will be determined only if the distance between that body part and an object is less than the predefined threshold. In some embodiments a status indicating that restraint of multiple or all body parts is required will be determined if the distance between at least one body part and an object is less than the predefined threshold. In further or alternative embodiments, the processing unit is arranged to calculate the velocity of a detected body part towards a detected object (for example from a series of measurements of the relative positions of body parts and objects obtained from a time series of images). In some such embodiments the processing unit is arranged to compare the calculated velocity to a predefined velocity threshold. The subject status may then be determined in dependence on the result(s) of the comparing. For example, in some embodiments a status indicating that restraint of a body part is required will be determined only if the velocity of the body part towards the object is more than the predefined velocity threshold. In some embodiments a status indicating that restraint of multiple or all body parts is required will be determined if the velocity of at least one body part towards an object is more than the predefined velocity threshold. An exemplary velocity threshold could be 2 m/s.

In some embodiments (i.e. embodiments in which the processing unit is arranged to receive sensor data in real time) the processing unit is arranged to determine a status of a subject in real time or near real time.

In some embodiments the determined subject status comprises a status value (which may, for example, take the form of a descriptive indication (e.g. asleep with low activity, asleep with high activity, awake with low activity, awake with high activity, delirious, violent, etc.) a numerical score (e.g. representing activity level), and/or a non-numerical status indication (e.g. a color corresponding to a low, medium or high risk that the patient will cause harm if not restrained). In some embodiments the determined subject status comprises a status value in respect of each of multiple factors, where a factor could be, e.g., activity level, medical condition, sleep/wake state, lucidity, etc. In some embodiments the determined subject status is indicated, e.g. by the restraint management apparatus or a device in communication with the restraint management apparatus. In some such embodiments indicating the determined subject status comprises displaying a message or visual status indication. In some embodiments indicating the determined subject status comprises emitting light of a particular color.

The processing unit is further arranged to determine, based on the determined subject status, a restraint parameter for a restraint device configured to restrain a body part of the subject, e.g. the restraint device 14. The determined restraint parameter can comprise, for example, one or more of: activation/inactivation of the restraint device (i.e. as a whole), activation/inactivation of a given restraining component of the restraint device, tightness/length of a given restraining component, duration of activation of the restraint device or of a given restraining component, etc. In some embodiments the processing unit is provided with a set of rules/relationships (e.g. stored in a memory of the restraint management device) relating restraint parameters to subject status and is arranged to use these rules/relationships in determining a restraint parameter. An example of such a rule could be, "if subject status=excessive hand movement, set hand restraining components to maximum tightness".

In embodiments where the restraint device can provide a controllable resistance to movement of a body part, the restraint parameter can indicate a level of resistance to movement to be provided by the restraint device.

In some embodiments the processing unit is arranged to determine a restraint parameter by applying at least one predefined criterion to the determined subject status. In some embodiments the predefined criterion comprises a set of conditions. In some embodiments the set of conditions comprises a time-based condition and a value-based condition. A value-based condition is defined such that whether or not a status value meets the condition depends on the value itself. A time-based condition, on the other hand, specifies a condition (e.g. a minimum) relating to the amount of time for which the status information has consistently met a value-based condition. Providing a time-based condition can be advantageous because some status factors may need to be consistently present for a duration of time before they can be considered to reliably indicate that a change in a restraint parameter (e.g. application of the restraint device to a currently unrestrained subject) is required. In some embodiments the set of conditions comprises a plurality of value-based conditions.

In some embodiments the processing unit is arranged to determine a restraint parameter using a function of the distance from a body part to an object in the environment, and/or of the velocity of a body part towards an object in the environment. An exemplary function based on distance x is set out below:

| | |
|---|---|
| $x \leq BT$ | $F_r = F_{max}$ |
| $x > RT$ | $F_r = F_{min}$ |
| Otherwise | $F_r = F_{max} + (BT - x)/(RT - BT) \cdot (F_{max} - F_{min})$ | where BT is a blocking threshold distance at which the movement of the body part is to be blocked (i.e. a maximum restraining force, $F_{max}$, is to be applied), RT is a restraining threshold distance beyond which a minimum restraining force ($F_{min}$) is to be applied. This function leads to the restraining force increasing from the minimum force at distances greater than RT up to the maximum force at distances of BT or less. An exemplary value for $F_{max}$ can be 1000 Newton (N), although any force that would prevent movement of the body part can be used. An exemplary value for $F_{min}$ can be 0.1 N, although any force that would allow free or reasonably free movement of the body part can be used. An exemplary value for BT can be 10 centimeters, and an exemplary value for RT can be 25 cm. The restraining force provided by the above function can be related to a restraint parameter. It will be appreciated that the above function is merely exemplary, and those skilled in the art will be aware of other types or forms of functions that can be used to relate distance and/or velocity to a restraining force.

In embodiments where the subject status comprises a status value for each of multiple factors, the at least one predefined criterion may be factor-specific. For example, in some embodiments the determined subject status comprises a status value for the factor "sleep/wake state" and a status value for the factor "activity level". In some such embodiments the processing unit is arranged to determine a restraint parameter based on both whether the sleep/wake state value is equal to a predefined value and whether the activity level value exceeds a predefined threshold. For example, in some such embodiments if the sleep/wake status value is "asleep" and the activity level is "medium" then the processing unit will determine that the restraining device should be used, but if the sleep/wake status value is "awake" and the activity level is "medium" then the processing unit will determine that the restraining device should not be used.

In some embodiments the processing unit includes a machine learning module, configured to use standard machine learning techniques to identify or generate rules, relationships, etc. relating restraint parameters to subject status. In some such embodiments the machine learning module is configured to apply machine learning techniques to historical data, e.g. historical subject status data, historical physiological measurement data, and/or historical restraint information (e.g. information about restraint parameters used and/or their appropriateness). In some embodiments (i.e. embodiments in which the processing unit is arranged to receive manually-input restraint parameters from the restraint device 14), the machine learning module is configured to generate rules/relationships relating restraint parameters to subject status based on manually-input restraint parameters received from the restraint apparatus. In some such embodiments the machine learning module is arranged to update existing rules/relationships based on manually-input restraint parameters received from the restraint apparatus. In some such embodiments the processing unit 12 is arranged to determine a restraint parameter based on rules or relationships generated or identified by the machine learning module.

In preferred embodiments the processing unit is arranged to determine a restraint parameter in real time or near real time. Advantageously this feature can prevent inappropriate restraint of a subject, and minimize the amount of time for which a subject is restrained. Conversely, it can ensure that restraint is applied rapidly when required, reducing the risk of harm to the subject.

The processing unit is further arranged to output a signal 12 based on the determined restraint parameter. In some embodiments the signal 12 comprises a control signal, and is output to the restraint device 14, e.g. by a communications module of the restraint management apparatus 10. In some such embodiments the signal 12 causes the restraint device to apply the determined restraint parameter. For example, in one example embodiment in which the determined restraint parameter comprises a specified length of a given restraint component of the restraint device 14, the output signal 12 comprises a control signal which causes the restraint device 14 to set the length of the given restraint component to be the specified length. In another example embodiment in which the determined restraint parameter indicates a level of resistance to movement to be provided by the restraint device 14, the output signal 12 comprises a control signal which causes the restraint device 14 to set the resistance to movement to the specified level of resistance. In some embodiments in which the signal 12 is output to the restraint device 14, the signal 12 is arranged to cause the restraint device 14 to display the determined restraint parameter, e.g. on a display associated with the restraint device 14. In some embodiments the signal comprises an instruction to a caregiver to implement the determined restraint parameter.

In some embodiments the signal comprises a control signal arranged to cause a message to be presented to the subject. Such a message could provide the subject with instructions and/or reassurance. A suitable message could say, for example, "Please calm down. A nurse will be with you shortly". In some embodiments the message to the subject comprises an audio message, e.g. generated by a loudspeaker comprised in or in communication with the restraint management device 10. In some embodiments the message to the subject comprises a visual message, e.g. displayed by a display comprised in or in communication with the restraint management device 10.

In some embodiments the processing unit is arranged to output the signal 12 after a predefined amount of time has passed since the processing unit last output a signal of the same type as the current signal 12 (e.g. in some embodiments an instruction or control signal arranged to cause adjustment of a particular restraint would comprise a first type of signal, and an instruction or control signal arranged to cause adjustment of a different restraint, a control signal arranged to generate an alarm, a warning message to a caregiver, etc. would each be considered to be a signal of a different type to the first signal). This can reduce the stress experienced by the subject, since if restraint parameters are changed too often this can confuse or surprise the subject.

In some embodiments the signal 12 comprises a control signal and is sent to a functional module of the restraint management apparatus 10. In such embodiments the control signal may be arranged, for example, to cause one or more of:
an alarm module to generate an alarm;
a subject feedback module to generate a message to the subject;
a communications module to generate a message to a caregiver;
a communications module to send a signal to a remote device;
a communications module to send a signal to the restraint management apparatus;
a display module to display information;
a lighting module to activate a light.

In some embodiments the processing unit is arranged to output a plurality of signals, for example a control signal to the restraint device 14 and a control signal to an alarm module of the restraint management apparatus 10 causing it to generate an alarm. In some embodiments the processing unit is arranged to output a signal 12 continuously, in real-time or near real-time. In some embodiments the processing unit is arranged to output a signal in response to a change in the determined parameter. In some embodiments the processing unit is arranged to output a signal 12 at periodic intervals.

The restraint device 14 can be any device arranged to restrain (i.e. to restrict the movement of) a body part of a subject. In some embodiments the restraint device 14 comprises multiple restraint components, each of which is arranged to restrain a particular body part. In some such embodiments, the restraint components comprise one or more straps (e.g. wrist straps, ankle straps, a waist strap, etc.). In some embodiments the restraint components comprise one or more tethers. In some embodiments the restraint device 14 comprises one or more bed rails. In some embodiments the restraint device 14 comprises a bed sheet or cover which can be adjustably tightened over the subject. In some embodiments the restraint device is attached to or integrated in a hospital bed. Preferably the restraint device 14 is arranged such that one or more restraint parameters (e.g. strap tightness/length, tether length, bed rail height, resistance to movement) are adjustable during use of the restraint device 14. Preferably, the restraint device is arranged to be as user friendly as possible. For example, straps can comprise a soft and/or padded material. Straps and/or tethers may be arranged to vary the resistance to movement in dependence on the length/tightness for variable fixation ranges. This can advantageously achieve a subtle braking of a moving body part rather than a hard stop, which can reduce the stress felt by the subject as a result of being restrained.

In some embodiments the restraint device 14 includes at least one sensor for acquiring sensor data. In some embodiments the restraint device 14 includes at least one sensor associated with each restraint component of the restraint device 14. The at least one sensor can comprise, for example, a strain gauge; an accelerometer; a position sensor. In some embodiments the restraint device 14 includes a sensor arranged to detect a parameter of the subject (e.g. position of a given body part, movement of a given body part, etc.). In some embodiments the restraint device 14 includes a sensor arranged to detect a parameter of the restraint device (e.g. position of a bed rail; length of a strap; tension in a strap/tether; whether or not a given restraint component is in use; etc.). In some embodiments in which the restraint device 14 includes at least one sensor, the restraint device 14 is arranged to output sensor data, e.g. to the restraint management apparatus 10 or to another remote device (such as a patient monitoring device or a hospital computer system).

The restraint device 14 can be an automated restraint device or a manually operated restraint device. A manually operated restraint device requires a human operator to adjust its restraint parameters. In embodiments where the restraint management device 10 is used in conjunction with a manually operated restraint device, the restraint management device is arranged to alert a caregiver to a change in the determined restraint parameter, so that the caregiver can implement the newly determined parameter. Although caregiver intervention to adjust the restraint device is still required, in such situations the restraint management system significantly reduces the burden on caregivers by reducing or removing the need for a caregiver to continuously monitor the status of subject.

An automated restraint device, on the other hand, is able to adjust one or more of its restraint parameters without input from a human operator, e.g. in response to a control signal received from the restraint management apparatus 10. Advantageously, the use of an automated restraint device in conjunction with a restraint management apparatus according to embodiments of the invention can enable the rapid (preferably real-time) adjustment of the nature and degree of restraint applied to a given subject, based on their current status. This can significantly reduce or even eliminate periods of inappropriate restraint. Preferably an automated restraint device is arranged such that restraint parameters can also be adjusted manually, e.g. via a user interface of the restraint device. In some embodiments, an automated restraint device is arranged such that a caregiver is required to approve/confirm a restraint parameter generated by the restraint management apparatus before the automated restraint device will apply that parameter. In some such embodiments the approval can be done remotely, via a device (such as a nurses' station, or portable electronic device of a caregiver) which is in communication with the restraint management apparatus and the restraint device.

Figure 2:
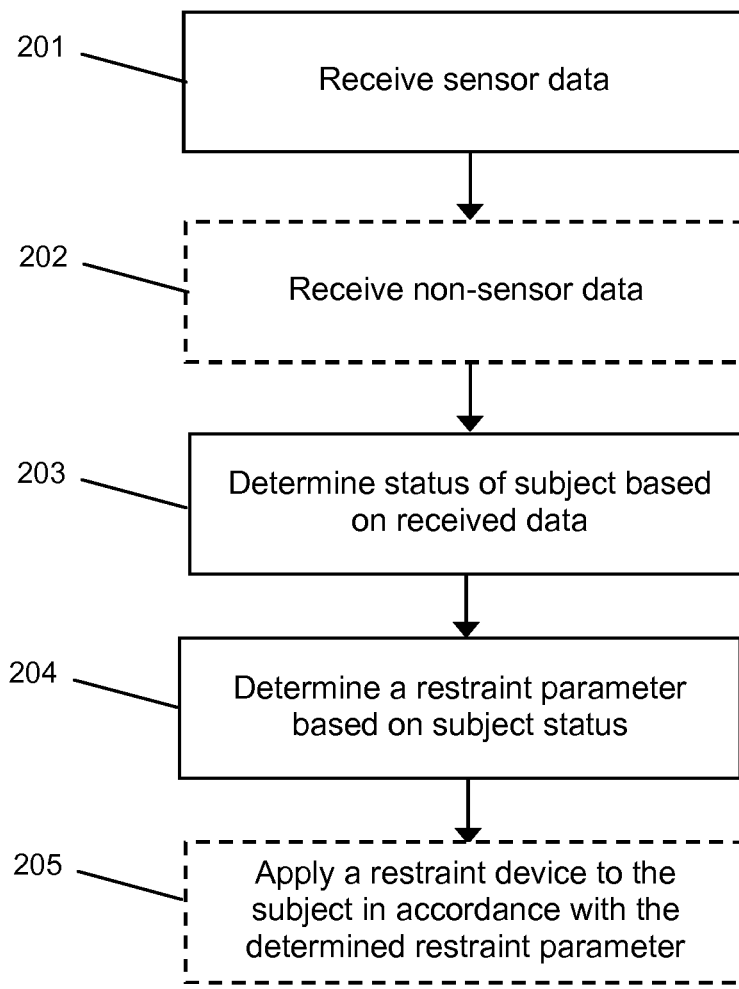
FIG. 2 is a flow chart illustrating a method for use in restraining a subject according to a general embodiment of the invention.

FIG. 2 shows an example of a method for use in restraining a subject, which can be implemented by the restraint management apparatus 10. In a first step 201 sensor data 16 is received, e.g. from one or more sensor devices, from a restraint device, from a user input module of the restraint management apparatus 10, from a remote electronic device, etc. In some embodiments the sensor data is received as a continuous stream. In some embodiments the sensor data is received periodically. In some embodiments the sensor data is received in response to a request previously sent to a sensor device/restraint device. In some embodiments the sensor data has been time-stamped at the time of its generation. In some embodiments the sensor data is time-stamped at the time of its receipt, e.g. by the processing unit of the restraint management apparatus 10. In some embodiments the received sensor data directly relates to a subject, in that it comprises measurements of a physiological characteristic of that subject. In some embodiments the received sensor data indirectly relates to a subject. For example, data which indirectly relates to a subject could comprise an image or audio recording of the subject's hospital room which includes the subject as well as their surroundings. In some embodiments the received sensor data is stored, e.g. in a memory of the restraint management apparatus 10.

In some embodiments an optional step 202 of receiving non-sensor data relating to the subject, e.g. from a user input module of the restraint management apparatus, a remote electronic device, etc. is performed. The subject-related non-sensor data can comprise, e.g. test results; a medical diagnosis; historical physiological characteristic data; clinical outcome data; treatment data, restraint data, etc. In some embodiments the received subject-related non-sensor data is stored, e.g. in a memory of the restraint management apparatus 10.

In step 203 a status of a subject (i.e. the subject to which the received sensor data either directly or indirectly relates) is determined based on the received sensor data, e.g. by the processing unit of the restraint management apparatus 10. In embodiments in which subject-related non-sensor data is received, a status of the subject is determined based additionally on the non-sensor data. In some such embodiments the received sensor data and the received non-sensor data are combined by a data fusion module of the processing unit of the restraint management apparatus 10. In some embodiments the combining comprises assigning one or more weights to the received sensor data and the received non-sensor data. For example, non-sensor data in the form of data input manually by a caregiver may be assigned a higher weight than sensor data. In some embodiments the non-sensor data can comprise a subject status manually input by a caregiver. In some such embodiments the performance of step 203 may comprise ignoring the received sensor data and determining the subject status to be the subject status received as non-sensor data. In some embodiments rules, e.g. generated by the machine learning module of the processing unit, are used in the combining. The determined subject status may take any of the forms described above in relation to the processing unit of the restraint management apparatus 10. Likewise, determining a status of a subject can comprise any of the processing techniques described above in relation to the processing unit of the restraint management apparatus 10.

In step 204 a restraint parameter is determined based on the determined subject status. The determined restraint parameter may take any of the forms described above in relation to the processing unit of the restraint management apparatus 10 or in relation to the restraint device 14. Likewise, determining a restraint parameter can comprise any of the processing techniques described above in relation to the processing unit of the restraint management apparatus. It is generally expected that a main consideration in the determining of a restraint parameter will be to maintain a balance between the comfort and freedom of the subject, and the clinical need to prevent certain adverse events occurring. The determined restraint parameter may be output in any suitable manner (including any of the manners described above in relation to the output signal 12) such that it can be implemented in restraining (or releasing) the subject.

In some embodiments the method includes the optional additional step 205 of applying a restraint device to the subject in accordance with the determined restraint parameter. The restraint device can have any or all of the features described above in relation to the restraint device 14. In some embodiments applying the restraint device comprises a caregiver manually setting a parameter of the restraint device to be equal to the determined parameter. In some embodiments applying the restraint device receiving a control signal based on a determined restraint parameter, and in response to the control signal, setting a parameter of its operation/configuration to be equal to the determined parameter.

Figure 3:
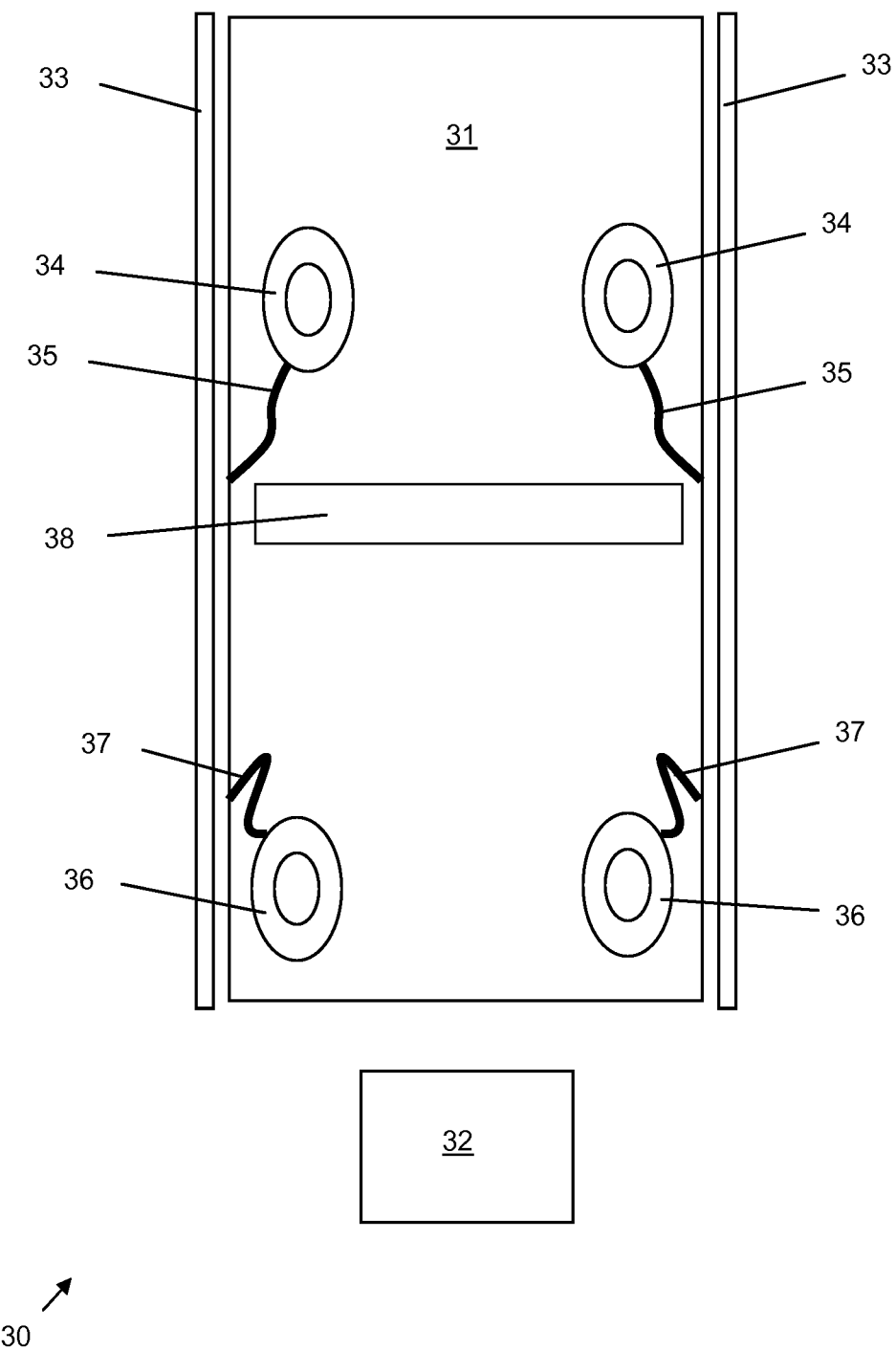
FIG. 3 is an illustration of an example restraint device for use with a restraint management apparatus according to the invention.

FIG. 3 shows a specific example of an automated restraint device 30 for use with a restraint management apparatus according to the invention. The restraint device 30 comprises various restraint components arranged on a hospital bed 31, and a control unit 32 which is in communication (either wired or wireless) with the restraint components so as to be able to send control signals to each of the restraint components. The restraint components comprise a pair of bed rails 33, the height of which can be adjusted in response to a control signal from the control unit 32 (e.g. by means of any suitable actuator). The restraint components also comprise a pair of wrist cuffs 34, each of which is connected to the hospital bed 31 by a tether 35. Similarly, the restraint components also comprise a pair of ankle cuffs 36, each of which is connected to the hospital bed 31 by a tether 37. The tightness of the wrist and ankle cuffs is manually adjustable (although it will be appreciated that embodiments are possible in which the tightness of the wrist and/or ankle cuffs can be automatically adjusted in response to a control signal from the control unit 32, e.g. by means of any suitable actuator). The length of each wrist and ankle tethers is individually and automatically adjustable in response to a control signal from the control unit 32, e.g. by means of any suitable actuator. The restraint components also comprise a waist strap 38. The waist strap 38 is arranged to be manually applied (although it will be appreciated that embodiments are possible in which the waist strap can be automatically applied) but once applied can be tightened automatically in response to a control signal from the control unit 32.

Where the restraint device is to provide a subtle braking of a moving body part rather than a hard stop as described above, the restraint components can comprise, e.g. a wrist strap, with one end of a connector string or cord attached thereto, and the other end attached to a spool inside a restraint actuator. The restraint actuator controls the freedom of movement of the spool, e.g. using a braking system (known to those skilled in the art of e.g. mechatronics). Depending on the configuration of the actuator system, the applied braking force can be proportional to the effective restraining force in the string or cord. The braking system may include a force sensor for force feedback control. In some embodiments, in the case of using a braking system as the main actuator, it can be important to maintain a minimal restraining force (e.g. $F_{min}$) in the string or cord at all times, to avoid slacking and tangling. This can be realized using a simple spring connected to the spool. Those skilled in the art will be aware of various types of restraint components that can be used to provide subtle braking of a moving body part.

The restraint device 30 further comprises a plurality of sensors (not shown) which are in communication (wired or wireless) with the control unit 32 and are arranged to send data to the control unit 32. The sensors comprise an accelerometer attached to each wrist cuff 34 and ankle cuff 36, a plurality of pressure sensors distributed over the base of the hospital bed 31, a position sensor attached to each bed rail 33, and a strain gauge attached to each tether 35, 37. The control unit is in communication with a restraint management apparatus (e.g. the restraint management apparatus 10 of FIG. 1) and is arranged to send data received from the plurality of sensors to the restraint management apparatus. In this embodiment the restraint management apparatus is provided a separate device to the restraint device, however; alternative embodiments are envisaged in which the restraint management apparatus is provided as a module of the control unit 32.

The control unit 32 is arranged to receive a control signal output by a restraint management apparatus, where the control signal is arranged to cause the restraint device to implement one or more restraint parameters determined by the restraint management apparatus. The control unit is arranged to, in response to receiving the control signal, implement a determined restraint parameter by sending a control signal to a restraint component arranged to cause an operational parameter of that restraint component to become equal to the determined restraint parameter. For example, in a case where the determined restraint parameter is "wrist tethers=50 cm", the control unit 32 sends a control signal to each of the wrist tethers 35, the control signal being arranged to cause an actuator associated with each of the wrist tethers to adjust the tether length to be equal to 50 cm.

The control unit 32 further comprises a user interface, via which restraint parameters can be manually input by a caregiver. The control unit 32 is arranged to, in response to receiving a manually-input restraint parameter, implement the manually-input restraint parameter by sending a control signal to a restraint component arranged to cause an operational parameter of that restraint component to become equal to the manually-input restraint parameter. The control unit 32 is also arranged to send the manually-input restraint parameter to the restraint management apparatus, e.g. for use by the restraint management apparatus in generating or updating rules/relationships relating subject status to restraint parameters, as described above in relation to FIG. 1. The control unit 32 is arranged to wait for a predetermined amount of time before implementing a change to an operating parameter of a given restraint component. In some embodiments the predetermined waiting time may be longer if the last change was performed to implement a manually-input restraint parameter than if the last change was performed to implement a restraint parameter determined by the restraint management apparatus. In some embodiments the control unit is arranged such that a manual input overrides signals received from the restraint management apparatus for a predetermined period of time.

Embodiments of the invention therefore advantageously enable the amount of time for which a subject is inappropriately restrained to be reduced, whilst also enabling restraints to be applied rapidly in response to potentially harmful movements by the subject, thus reducing their risk of harming them self, other people, or medical equipment. Embodiments of the invention can facilitate automatic restraint implementation and adjustment, and therefore also have the potential to significantly reduce the burden on caregivers, by reducing or eliminating the requirement for caregiver involvement in both monitoring a subject and adjusting restraint devices.

While the invention has been illustrated and described in detail in the drawings and foregoing description, such illustration and description are to be considered illustrative or exemplary and not restrictive; the invention is not limited to the disclosed embodiments. Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A restraint management system for reducing a risk of damage to medical equipment and/or another person, the restraint management system comprising:
   a restraint device comprising a wrist strap or wrist cuff, the restraint device configured to restrain a hand of a subject; and
   a restraint management apparatus having a processing unit arranged to:
      receive one or more types of sensor data;
      determine a status of the subject based on the received sensor data, wherein the status comprises a velocity of the hand of the subject towards medical equipment and/or another person in the environment around the subject;
      determine, based on the determined subject status, a restraint parameter for the restraint device, wherein the restraint parameter indicates a level of resistance to movement to be provided by the restraint device, and wherein the restraint parameter is determined by a calculation such that the level of resistance to movement provided by the restraint device increases as the velocity of the hand towards the medical equipment and/or another person increases; and
      output a signal based on the determined restraint parameter;
   wherein the restraint device is arranged to apply a restraint to the subject or alter a parameter of a restraint applied to the subject in response to the signal received from the restraint management apparatus.

2. The restraint management system of claim 1, wherein the processing unit is further arranged to receive one or more types of non-sensor data relating to the subject and to determine a status of a subject based additionally on the received non-sensor data.

3. The restraint management system according claim 1, wherein the processing unit comprises a memory containing one or more predefined signatures, each predefined signature relating to a particular type of feature, and wherein the processing unit is arranged to determine a status of a subject by comparing the received data to the one or more predefined signatures to detect one or more features in the received sensor data.

4. The restraint management system according to claim 1, wherein the processing unit is arranged to determine a status of a subject such that the determined status comprises a status value for one or more factors, wherein each status value comprises one or more of: a descriptive indication; a numerical score; a non-numerical level indication.

5. The restraint management system according to claim 4, wherein the processing unit comprises a memory containing rules relating subject status values to restraint parameters, and is arranged to determine a restraint parameter by applying one or more of the rules to the determined subject status value.

6. The restraint management system according to claim 5, wherein the processing unit comprises a machine learning module, wherein the rules have been generated by the machine learning module based on historical data relating to the subject, wherein the processing unit is arranged to receive a restraint parameter which has been manually-input to a restraint device, and wherein the machine learning module is arranged to update the generated rules based on the received manually-input restraint parameter.

7. The restraint management system according to claim 1, wherein the processing unit is arranged to determine a restraint parameter such that the determined restraint parameter comprises one of:
  activation of a restraint device;
  inactivation of a restraint device;
  activation of a given restraining component of a restraint device;
  inactivation of a given restraining component of a restraint device;
  tightness of a given restraining component of a restraint device;
  length of a given restraining component of a restraint device;
  duration of activation of a restraint device;
  duration of activation of a given restraining component of a restraint device.

8. The restraint management system according to claim 1, wherein the processing unit is arranged to output a signal comprising one or more of:
  a control signal to an automated restraint device arranged to cause the automated restraint device to apply the determined restraint parameter;
  a signal to a device associated with a caregiver, the signal comprising an instruction to the caregiver to implement the determined restraint parameter;
  a control signal to an alarm module of the restraint management apparatus arranged to cause the alarm module to generate an alarm in dependence on the determined restraint parameter;
  a control signal to a display module of the restraint management apparatus arranged to cause the display module to display information in dependence on the determined restraint parameter;
  a control signal to a subject feedback module arranged to cause the subject feedback module to generate a message to the subject;
  a control signal to a lighting module arranged to cause the lighting module to activate a light.

9. The restraint management system according to claim 1, wherein the processing unit is arranged to output the signal after a predefined amount of time has passed since the processing unit last output a signal of the same type as the signal.

10. The restraint management system according to claim 1, wherein the restraint device is further arranged to:
  receive a manually-input restraint parameter;
  in response in response to a signal received from the restraint management apparatus, apply a restraint to the subject or alter a parameter of a restraint applied to the subject; and
  transmit a signal containing the manually-input restraint parameter to the restraint management apparatus.

11. A method for use in restraining a subject to reduce a risk of damage to medical equipment and/or another person, the method comprising:
  providing a restraint device comprising a wrist strap or wrist cuff, the restraint device configured to restrain a hand of a subject;
  receiving, by a restraint management apparatus, one or more types of sensor data;
  determining, by a processing unit of the restraint management apparatus, a status of the subject based on the received sensor data, wherein the status comprises a velocity of the hand of the subject towards medical equipment and/or another person in the environment around the subject;
  determining, by the processing unit of the restraint management apparatus, based on the determined subject status, a restraint parameter for the restraint device, wherein the restraint parameter indicates a level of resistance to movement to be provided by the restraint device, and wherein the restraint parameter is determined by a calculation such that the level of resistance to movement provided by the restraint device increases as the velocity of the hand towards the medical equipment and/or another person increases;
  outputting a signal based on the determined restraint parameter from the restraint management apparatus; and
  applying a restraint to the subject or altering a parameter of a restraint applied to the subject in response to the signal from the restraint management apparatus.

12. The method according to claim 11, wherein the received sensor data comprises one or more of:
  an image including a subject;
  an image including a subject and one or more objects in the vicinity of the subject;
  audio data including sounds generated by a subject;
  accelerometer data obtained by an accelerometer worn by a subject;
  measurements of one or more physiological characteristics of a subject;
  restraint-related data obtained by a sensor associated with a restraint device;
  pressure data obtained by a bed sensor;
  bed rail position data obtained by a bed rail sensor.

13. The method according to claim 11, wherein the received sensor data comprises an image including a subject and one or more objects, and wherein determining a status of a subject comprises:

determining a position of the hand of the subject;

determining a position of medical equipment and/or another person in the image;

calculating a distance between the hand and the medical equipment and/or another person; and comparing the calculated distance to a predetermined threshold.

14. The method according to claim 11, wherein the received sensor data comprises a series of images including a subject and one or more objects, and wherein determining a status of a subject comprises:

determining a position of the hand of the subject in each of the images;

determining a position of medical equipment and/or another person in each of the images;

calculating a distance between the hand and the medical equipment and/or another person in each of the images;

calculating a velocity of the hand towards the medical equipment and/or another person from the calculated distances; and comparing the calculated velocity to a predetermined velocity threshold.

15. A restraint management system for reducing a risk of damage to another person, the restraint management system comprising:

a restraint device comprising a wrist strap or wrist cuff, the restraint device configured to restrain a hand of a subject; and a restraint management apparatus having a processing unit arranged to:

receive one or more types of sensor data;

determine a status of the subject based on the received sensor data, wherein the status comprises a velocity of the hand of the subject towards another person in the environment around the subject;

determine, based on the determined subject status, a restraint parameter for the restraint device, wherein the restraint parameter indicates a level of resistance to movement to be provided by the restraint device, and wherein the restraint parameter is determined such that the level of resistance to movement provided by the restraint device increases as the velocity of the hand towards the another person increases; and output a signal based on the determined restraint parameter;

wherein the restraint device is arranged to apply a restraint to the subject or alter a parameter of a restraint applied to the subject in response to the signal received from the restraint management apparatus.

* * * * *